(12) United States Patent
Azuma et al.

(10) Patent No.: US 7,321,054 B2
(45) Date of Patent: Jan. 22, 2008

(54) METHOD OF PRODUCING POLY(ORTHO-METHYLPHENOL)

(75) Inventors: Rie Azuma, Wakayama (JP); Tadashi Hiramine, Wakayama (JP)

(73) Assignee: Honshu Chemical Industry Co., Ltd., Tokyo (JP)

( * ) Notice: Subject to any disclaimer, the term of this patent is extended or adjusted under 35 U.S.C. 154(b) by 0 days.

(21) Appl. No.: 11/671,901

(22) Filed: Feb. 6, 2007

(65) Prior Publication Data

US 2007/0197832 A1    Aug. 23, 2007

(30) Foreign Application Priority Data

Feb. 7, 2006   (JP) .............................. 2006-030185

(51) Int. Cl.
*C07C 309/00*   (2006.01)
(52) U.S. Cl. ..................................... 562/113
(58) Field of Classification Search ..................... None
See application file for complete search history.

(56) References Cited

FOREIGN PATENT DOCUMENTS

| | | |
|---|---|---|
| JP | 49-55635 | 5/1974 |
| JP | 2003-238470 | 8/2003 |

OTHER PUBLICATIONS

Hubacher (Journal of the American Chemical Society (1961) vol. 61, p. 2664).*
Max H. Hubacher, "3,3'- Dimethyl-4,4'-dihydroxybenzophenone," Journal of American Chemical Society vol. 61, 1961 pp. 2664-2665.
M. Gombero, et al., $3^1$, $3^2$, $3^3$-Trimethyl-Aurin (Ortho-Cresaurin) and $3^1$, $3^2$, $3^3$—Trimethyl-$N^1$, $N^2$, $N^3$—Triphenyl-Para-Rosaniline (Triphenyl-Ros-Ortho-Toluidine), Journal of American Chemical Society vol. 47, Jul. 1925 pp. 2022-2033.

* cited by examiner

*Primary Examiner*—Yvonne Eyler
*Assistant Examiner*—Kellette Gale
(74) *Attorney, Agent, or Firm*—Knobbe, Martens, Olson & Bear LLP

(57) ABSTRACT

Poly(ortho-methylphenol) is obtainable at high purities and yields using industrial processes by causing a secondary amine and formaldehyde to react with a polyphenol (first step), and then breaking down the aminomethyl group of the obtained poly(ortho-aminomethyl)phenol by means of hydrogenolysis in the presence of a hydrogenation catalyst (second step).

12 Claims, No Drawings

METHOD OF PRODUCING POLY(ORTHO-METHYLPHENOL)

BACKGROUND OF THE INVENTION

1. Field of the Invention

The present invention relates to a method of producing a poly(ortho-methylphenol), and more specifically relates to a production method to easily obtain, at high purities and yields using industrial processes, a poly(ortho-methylphenol) useful as a material for liquid crystal polyester resin, polyarylate resins, polycarbonate resins, epoxy resins and other synthetic resins offering high heat resistance and good molding property, as well as materials for high-functional compounds such as liquid crystal display elements and photo-resists.

2. Description of the Related Art

Among the conventional methods of producing a polymethylphenol, methods known to produce bispoly(methylphenol) include one relating to the production of 4,4'-dihydroxy-3,3'-dimethyldiphenyl ether, wherein 4,4'-dihydroxyphenyl ether is used as a raw material, which is formylated and then methylated to obtain the target, or 4,4'-dihydroxy phenyl ether is alkylated, formylated, methylated and then finally dealkylated to obtain the target (Japanese Patent Laid-open No. 2003-238470). However, the aforementioned method requires a long, complex process, and the yield of the target is low.

Meanwhile, a method to produce dimethyl-dihydroxydiphenyl ether is known, wherein 2-methylhydroquinone is used as a raw material, which is dehydrated and dimerized in the presence of a montmorillonite catalyst to obtain the target (Japanese Patent Laid-open No. Sho 49-55635).

Similarly as a method to produce dimethyl-dihydroxydiphenyl ether, one wherein 2-methylhydroquinone is dehydrated and dimerized in the presence of a synthetic mica catalyst to obtain the target is known (Japanese Patent Laid-open No. Sho 59-206326). However, the aforementioned methods require expensive materials and offer low conversion ratios, and the target is obtained only as a mixture containing isomers.

Furthermore, a method to produce 3,3'-dimethyl-4,4'dihydroxybenzophenone is presented in the Journal of American Chemical Society, Vol. 61, 2664 (1961), in which orthocresol phthalein is used as a raw material, which is alkali hydrolyzed with KOH to obtain the target. However, the aforementioned method also requires an expensive material that cannot be easily produced through industrial processes, and the yield is low.

Also among methods to produce trispoly(methylphenol), a method to produce 3,3',3"-trimethyl-4,4',4"-trihydroxyphenylmethane is presented in the Journal of American Chemical Society, Vol. 47, 2022 (1925), in which orthocresol and carbon tetrachloride are used as raw materials, which are reacted with each other in the presence of a zinc chloride catalyst to obtain 3,3',3"-trimethylaurine (O-Cresaurin) and then this compound is reduced to finally obtain the target. However, the aforementioned method requires a long process, and the yield of the target is low. Therefore, none of the methods described above provides an economical production method that can be used advantageously in industrial processes to produce poly(ortho-methylphenol).

SUMMARY OF THE INVENTION

The present invention was developed with the purpose of solving the aforementioned problems associated with the production of a poly(ortho-methylphenol), and consequently an object of the present invention is to provide a method of producing a poly(ortho-methylphenol), especially a bis(ortho-methylphenol), a tris(ortho-methylphenol) and a tetrakis(ortho-methylphenol), at high yields and purities, by using materials that can be easily produced through industrial processes and by causing reactions under reaction conditions that can be easily implemented through industrial processes.

An embodiment of the present invention provides a method of producing a poly(ortho-methylphenol) expressed by general formula (2) below, characterized by causing formaldehyde to react with a polyphenol compound expressed by general formula (1) in the presence of a secondary amine to obtain a poly(ortho-aminomethyl)phenol (first step), and then breaking down the aminomethyl group of the obtained poly(ortho-aminomethyl)phenol by means of hydrogenolysis in the presence of a hydrogenation catalyst (second step).

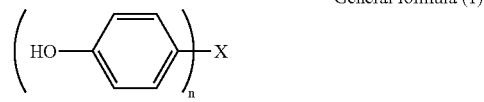

General formula (1)

(In the formula, X represents a —O— group, —S— group, carbonyl group, aromatic hydrocarbon group or saturated hydrocarbon group of carbon number 1 to 12, while n represents an integer of 2 to 4.)

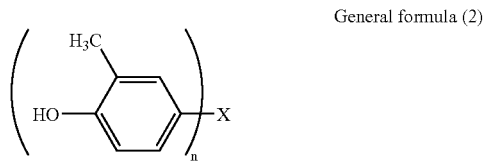

General formula (2)

(In the formula, X and n represents the same things as those in general formula (1).)

According to an embodiment, a poly(ortho-methylphenol) can be obtained at high yields and purities by using readily available a polyphenol as a starting material and based on two simple steps that can be easily implemented through industrial processes.

DETAILED DESCRIPTION OF THE PREFERRED EMBODIMENT

Under the method of producing poly(ortho-methylphenol) proposed by an embodiment of the present invention, a polyphenol compound expressed by general formula (1) below are used as a starting material.

Under the production method proposed by an embodiment of the present invention, the purities of a polyphenol compound that are used as a starting material is not specifically limited, and a polyphenol compound of industrial product grades or those of lower-end product grade with a purity of, say, 95% or below but 80% or above can be used.

Under the production method proposed by an embodiment of the present invention, the target poly(ortho-methylphenol) expressed by general formula (2) below is obtained by sequentially implementing the first step in which a polyphenol compound expressed by general formula (1) below is caused to react with formaldehyde in the presence of a secondary amine to obtain a poly(ortho-aminomethyl)phenol, and the second step in which the aminomethyl group of the obtained poly(ortho-aminomethyl)phenol is broken down by means of hydrogenolysis in the presence of a hydrogenation catalyst.

The polyphenol compound expressed by general formula (1) used in the aforementioned first step is expressed by the formula specified below.

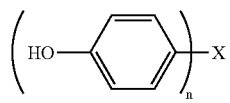

General formula (1)

X represents a —O— group, —S— group, carbonyl group, aromatic hydrocarbon group or saturated hydrocarbon group of carbon number 1 to 12. Saturated hydrocarbon groups of carbon number 1 to 12 include bivalent, trivalent or tetravalent saturated hydrocarbon groups of straight-chain, branched-chain or cyclic type. Specifically, saturated hydrocarbon groups where X is bivalent include, for example, chain-type alkylidene groups or alykylene groups such as methylene group, ethylene group, 1,3-propylene group, isopropylidene group, 1-methyl-1,1-propylidene group, 1,2-dimethyl-1,1-propylidene group, 2-methyl (1-methyl ethyl)-1,1-propylidene group, 1-methyl-1,1-heptylidene group, and 1,1-hexylidene group; and cycloalkylidene groups or cycloalkylene groups such as 1,1-cyclopentylene group, 1,1-cyclohexylidene group, 1,4-cyclohexylene group.

Saturated hydrocarbon groups where X is trivalent include trivalent hydrocarbon groups of branched-chain or straight-chain type such as methine group (group 1), ethylidyne group (group 2), propylidyne group, propane-1,2-2-tolyl group (group 4), butane-1,3,3-tolyl group (group 5); and trivalent hydrocarbon groups of cyclic type such as cyclopentane-1,1,4-tolyl group, cyclohexane-1,1,4-tolyl group (group 3).

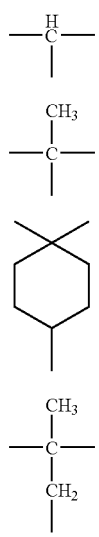

Group 1

Group 2

Group 3

Group 4

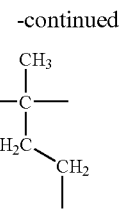

Group 5

Saturated hydrocarbon groups where X is tetravalent include tetravalent hydrocarbon groups of branched-chain or straight-chain type such as methane-tetrayl group (group 8), ethane-1,1,2,2-tetrayl group (group 6), propane-1,2,2,3-tetrayl group; and tetravalent hydrocarbon groups of cyclic type such as cyclohexane-1,1,4,4-tetrayl group (group 7).

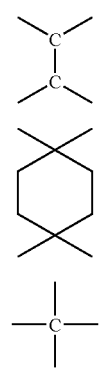

Group 6

Group 7

Group 8

Specific examples of aromatic hydrocarbon groups include phenylene group, benzene-triyl group, benzene-tetrayl group and biphenylene group, among others.

Also, n represents an integer of 2 to 4 that changes in accordance with the free valence of X. If X is a bivalent group, n is 2. If X is a trivalent group, n is 3. Similarly, if X is a tetravalent group, n is 4. Accordingly, n is 2 when X is a bivalent —O— group, —S— group or carbonyl group.

Specific examples of polyphenol compounds expressed by general formula (1) above include the following:
4,4'-dihydroxydiphenyl ether
4,4'-dihydroxydiphenyl sulfide
4,4'-dihydroxydiphenyl ketone
Tris(4-hydroxyphenyl)methane
1,3,3-tris(4-hydroxyphenyl)butane
1,1,4-tris(4-hydroxyphenyl)cyclohexane
1,1,1-tris(4-hydroxyphenyl)ethane
4,4'-dihydroxydiphenylmethane
1,1-bis(4-hydroxyphenyl)ethane
1,1-bis(4-hydroxyphenyl)propane
1,1-bis(4-hydroxyphenyl)butane
2,2-bis(4-hydroxyphenyl)propane
2,2-bis(4-hydroxyphenyl)butane
2,2-bis(4-hydroxyphenyl)-3-methylpentane
1,1,4,4-tetrakis(4-hydroxyphenyl)cyclohexane
1,1,2,2-tetrakis(4-hydroxyphenyl)ethane
Tetrakis(4-hydroxyphenyl)methane
1,4-bis(4-hydroxyphenyl)cyclohexane
4,4''-dihydroxy-p-terphenyl The formaldehyde used in the aforementioned first step is not limited to a specific form of use. For example, 35% aqueous formalin solution, paraform or other form of formaldehyde may be used.

Also, formaldehyde should normally be used in the range of from moles equivalent to the moles of the hydroxyl group in the polyphenol compound (n moles in the general formula (1)) to twice (preferably 1.5 times, or more preferably 1.2 times) the moles of the hydroxyl group in the polyphenol compound per one mole of the polyphenol compound.

As for the secondary amine used in the first step of the production method proposed by embodiments of the present invention, specific examples include dimethylamine, diethylamine, diarylamine, diisopropylamine, diisobutylamine, dipropylamine, dibutylamine, di-2-ethylhexylamine, di-sec-butylamine, dipentylamine, dihexylamine, methylethylamine, methylpropylamine, ethylpropylamine and other acyclic secondary amines; piperidine, pyrrolidine, ethyleneimine, morpholine and other cyclic secondary amines; diethanolamine and other dialcohol amines; dicyclohexyl amine, N-methylcyclohexylamine, N-ethylcyclohexylamine, N-propylcyclohexylamine, N-butylcyclohexylamine, N-isopropylcyclohexylamine, N-isobutylcyclohexylamine, N-sec-butylcyclohexylamine, N-hexylcyclohexylamine, N-2-ethylhexylcyclohexylamine and other secondary amines containing alicyclic group; and diphenylamine, N-methylaniline, N-ethylaniline, N-propylaniline, N-butylaniline, N-isopropylaniline, N-isobutylaniline, N-sec-butylaniline, N-hexylaniline, N-2-ethylhexylaniline and other secondary aromatic amines. Among others, cyclic amines can be used favorably, of which morpholine is particularly favorable.

The aforementioned secondary amine should normally be used in the range from moles equivalent to the moles of the hydroxyl group in the polyphenol compound (n moles in the general formula (1)) to twice (preferably 1.5 times, or more preferably 1.25 times) the moles of the hydroxyl group in the polyphenol per one mole of the polyphenol compound.

Also, it is desirable that the mole ratio of the aforementioned secondary amine and formaldehyde be close to equal, or 1:1 to 1.2:1.

Meanwhile, a solvent or solvents may or may not be used in the first step of the production method proposed by embodiments of the present invention. For example, no solvent is required if the reaction liquids are fluid. If a solvent or solvents are to be used, examples include benzene, toluene, xylene, mesitylene and other aromatic hydrocarbons; hexane, heptane, cyclohexane and other aliphatic hydrocarbons; methanol, ethanol, 2-propanol and other alcohols; and water. These solvents may be used alone, or two or more solvents may be combined. These solvents are normally used in the range of 1 to 1,000 parts by weight, or preferably in the range of 50 to 500 parts by weight, or more preferably in the range of 100 to 200 parts by weight, with respect to 100 parts by weight of polyphenol. In the aforementioned first step under an embodiment of the present invention, use of toluene or other aromatic hydrocarbon solvent is desirable, because then poly(ortho-aminomethyl) phenol can be easily obtained in the form of crystal at high purities and yields only through reaction, cooling and crystallization, where the refinement step based on crystallization, etc., can be implemented easily.

The reaction temperature should normally be in the range of −50° C. to 150° C. If the reaction temperature is too high, byproducts where both ortho positions relative to the hydroxy group bound to the phenyl nucleus are amino-methylated will increase, which is not desirable.

An appropriate reaction temperature should be selected based on the material polyphenol and solvent used, among others. However, when X is an ether group or carbonyl group in the material polyphenol expressed by general formula (1), for example, then the reaction temperature should be in the range of 50° C. to 100° C., or preferably in the range of 70° C. to 90° C. Similarly when X is a saturated hydrocarbon group and an aromatic hydrocarbon solvent is used, then the reaction temperature should normally be in the range of 20° C. to 60° C., or preferably in the range of 30° C. to 50° C., in order to improve the selectivity of the target by causing the target to crystallize and precipitate during the reaction.

The reaction in the aforementioned first step is so-called the Mannich reaction, where a dehydration/condensation reaction of formaldehyde, secondary amine and polyphenol converts the hydroxy group-substituted phenyl ring into a tertiary amino methyl. In this reaction, the hydrogen bound to the carbon atom in each ortho position next to the hydroxyl group, which in turn is bound to the phenol ring of the polyphenol, is active, and therefore amino-methylation can be easily caused by the Mannich reaction. Once one side is amino-methylated, however, the hydrogen atom in the same aromatic ring stabilizes and further amino-methylation is hindered. Also, because polyhydroxyphenyls where only one ortho position is amino-methylated have low solubility, only diaminomethylate precipitates as crystal during the reaction and thus further amino-alkylation is hindered. It is considered that for these reasons only the ortho position on one side is amino-methylated at high selectivity.

The reactions in the aforementioned first step and second step are expressed by the reaction formulas specified below when, for example, 4,4'-dihydroxydiphenyl ether is caused to react with formaldehyde and morpholine to obtain 3,3'-dimorpholinomethyl-4,4'-dihydroxydiphenyl ether, and then the morpholino methyl group is broken down by means of hydrogenolysis using a hydrogenation catalyst to obtain 3,3'-dimethyl-4,4'-dihydroxydiphenyl ether.

First step

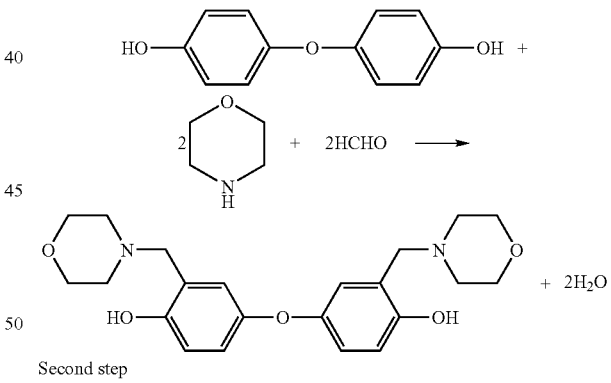

Second step

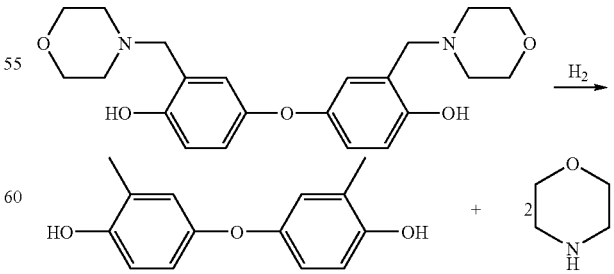

In the amino-methylation reaction explained above (first step), the order in which the materials are added is not specifically limited. However, the poly(ortho-aminomethyl)

phenol can be obtained at high selectivity if, for example, the material polyphenol is added to an organic solvent such as toluene in an ambience of inactive gas, after which the mixture is agitated, the secondary amine is added, and then the temperature is raised to approx. 30 to 90° C. to add formaldehyde, or the secondary amine and formaldehyde are added simultaneously, and the mixture is agitated to cause reaction.

The reaction selectivity is normally around 60 to 90%.

The obtained reaction mixture may be used directly, or after condensed through distillation, etc., as the material for the reaction in the second step to be carried out subsequently. Alternatively, a reaction product, or specifically poly(ortho-aminomethyl)phenol, may be separated from the reaction mixture by means of recrystallization, etc. and refined to high purity, to be used as the material for the reaction in the second step to be carried out subsequently. As for the method to refine the target from the reaction mixture, if crystal is precipitated during the reaction the crystal can be cooled directly and filtered to obtain the target. Or, the reaction solvent in the reaction mixture may be condensed, after which another solvent is added to achieve refinement through crystallization. Byproducts may sometimes precipitate first during crystallization, and in such cases impurities should ideally be filtered and removed.

Another approach is to add a solvent to the reaction mixture to dissolve the target in the oil layer, and then wash the oil layer in water and remove the materials of low boiling points (amine and formaldehyde) together with the solvent through distillation, in order to obtain the target in form of a liquid residue of the distillation process. Such operation may be performed several times, or two or more similar operations may be combined, as necessary.

Under the production method proposed by an embodiment of the present invention, the aminomethyl group of the poly(ortho-aminomethyl)phenol obtained by the reaction in the aforementioned first step is broken down by means of hydrogenolysis in the presence of a catalyst during the reaction in the second step. This allows the target of an embodiment of the present invention, or poly(ortho-methylphenyl) expressed by general formula (2) above, to be obtained at high purity and yield.

In general formula (2) above, X and n represent the same things as those in general formula (1), and therefore the poly(ortho-methylphenol) corresponding to the material polyphenol used can be obtained.

To be specific, the target poly(ortho-methylphenol) that can be obtained by the production method proposed by an embodiment of the present invention include the following:
3,3'-dimethyl-4,4'-dihydroxydiphenyl ether
3,3'-dimethyl-4,4'-dihydroxydiphenyl sulfide
3,3'-dimethyl-4,4'-dihydroxydiphenyl ketone
Tris(3-methyl-4-hydroxyphenyl)methane
1,3,3-tris(3-methyl-4-hydroxyphenyl)butane
1,1,4-tris(3-methyl-4-hydroxyphenyl)cyclohexane
1,1,1-tris(3-methyl-4-hydroxyphenyl)ethane
3,3'-dimethyl-4,4'-dihydroxydiphenylmethane
1,1-bis(3-methyl-4-hydroxyphenyl)ethane
1,1-bis(3-methyl-4-hydroxyphenyl)propane
1,1-bis(3-methyl-4-hydroxyphenyl)butane
2,2-bis(3-methyl-4-hydroxyphenyl)propane
2,2-bis(3-methyl-4-hydroxyphenyl)butane
2,2-bis(3-methyl-4-hydroxyphenyl)-3-methylpentane
1,1,4,4-tetrakis(3-methyl-4-hydroxyphenyl)cyclohexane
1,1,2,2-tetrakis(3-methyl-4-hydroxyphenyl)ethane
Tetrakis(3-methyl-4-hydroxyphenyl)methane
3,3"-dimethyl-4,4"-hydroxy-p-terphenyl Of the above, 3,3'-dimethyl-4,4'-dihydroxydiphenyl ether, tris(3-methyl-4-hydroxyphenyl)methane, 1,3,3-tris(3-methyl-4-hydroxyphenyl)butane and 1,1,4-tris(3-methyl-4-hydroxyphenyl)cyclohexane can be used favorably, of which 3,3'-dimethyl-4,4'-dihydroxydiphenyl ether is particularly favorable.

During the reaction in the second step where the aforementioned poly(ortho-aminomethyl)phenols are selectively broken down by means of hydrogenolysis in the presence of a hydrogenation catalyst, the hydrogenation catalyst may be any known hydrogenation catalyst. Examples include Raney nickel, reduced nickel, substrate-supported nickel catalyst and other nickel catalysts; Raney cobalt, reduced cobalt, substrate-supported cobalt catalyst and other cobalt catalysts; Raney copper and other copper catalysts; palladium oxide, palladium black, carbon-supported palladium catalyst and other palladium catalysts; platinum black, carbon-supported platinum and other platinum catalysts; rhodium catalysts; ruthenium catalysts; chromium catalysts; and copper chromium catalysts. Among these, palladium and other platinum group catalysts can be used favorably, of which palladium catalysts and palladium-platinum mixed catalysts are particularly favorable.

As for the aforementioned palladium catalysts, specific examples include a substrate-supported palladium catalyst where approx. 0.1 to 10 percent by weight of palladium metal is supported on a substrate made of carbon, alumina, active white clay, etc.; palladium catalyst containing acid component where an acid component acting as a co-catalyst is supported on a substrate along with a palladium component; catalyst combining a palladium catalyst where a palladium component acting as a catalytic component is supported on a substrate, with an acid component acting as a co-catalyst; and noble metal complex catalysts such as palladium chloride, palladium acetate, tris-triphenylphosphinerhodium chloride, etc. Palladium catalysts used in an embodiment of the present invention are not limited to any specific form, and those of powder, tablet or any other form may be used as deemed appropriate.

According to an embodiment of the present invention, the quantity of hydrogenation catalyst should normally be in the range of 0.5 to 10 parts by weight, or preferably in the range of 1.0 to 5.0 parts by weight, with respect to 100 parts by weight of poly(ortho-aminomethyl)phenol. Although co-catalysts are not required, it is desirable that an acid component be used as a co-catalyst. Such co-catalyst should normally be used in the range of 0.01 to 100 parts by weight, or preferably in the range of 0.05 to 10 parts by weight, with respect to 100 parts by weight of poly(ortho-aminomethyl) phenol.

The specific examples of the aforementioned acid component include formic acid, acetic acid, propionic acid, oxalic acid and other organic acids; and hydrochloric acid, hydrobromic acid, hydroiodic acid, perchloric acid, sulfuric acid and other mineral acids.

When the poly(ortho-aminomethyl)phenol is selectively broken down by means of hydrogenolysis in the presence of any such hydrogenation catalyst, it is desirable that hydrogen replacement be performed after replacing the system with an inactive gas such as nitrogen gas or argon gas.

The hydrogenation reaction should normally be carried out at temperatures in the range of 20 to 180° C., or preferably in the range of 60 to 140° C., and at hydrogen pressures in the range of 0.1 to 1.5 MPa (gauge pressure), or preferably in the range of 0.2 to 1 MPa (gauge pressure). Ideally, hydrogen should be supplied into the system to maintain a constant hydrogen pressure in the system during the reaction, with the reaction stopped once hydrogen absorption in the system stops. The reaction time should normally be in the range of 0.5 to 20 hours, or preferably in the range of 2 to 15 hours.

A solvent or solvents may be used in the aforementioned hydrogenation reaction, if necessary. If any solvent is used, it may be water, alcohols, esters, hydrocarbons, ethers, acetic acid and other organic acids, or morpholine and other organic amines.

In the aforementioned hydrogenation reaction step, use of an organic acid or alcohol as a solvent during the reaction will enhance the reaction selectivity. Also, since the starting material and target product easily dissolve in such solvents, reaction operation will also be facilitated.

Specific examples of the aforementioned solvents include acetic acid, propionic acid and other carbonic acids; and methyl alcohol, ethyl alcohol, n-propyl alcohol, isopropyl alcohol, n-butyl alcohol, isobutyl alcohol, s-butyl alcohol, t-butyl alcohol, n-amyl alcohol, isoamyl alcohol, n-hexyl alcohol, n-heptyl alcohol, n-octyl alcohol and other aliphatic alcohols. Among these, acetic acid and other lower saturated aliphatic carbonic acids and methyl alcohol, ethyl alcohol, isopropyl alcohol and other primary saturated aliphatic alcohols can be used favorably. These solvents may be used alone, or two or more solvents may be combined.

The quantity of such solvents should normally be in the range of 50 to 1,000 parts by weight, or preferably in the range of 100 to 300 parts by weight, with respect to 100 weight by parts of poly(ortho-aminomethyl)phenol.

During the hydrogenolysis reaction in the aforementioned second step, a poly(ortho-methylphenol) can be obtained by, for example, introducing to an autoclave the poly(ortho-aminomethyl)phenol obtained in the first step together with a solvent and a hydrogenation catalyst, and then causing reaction at temperatures of 90 to 130° C. while maintaining the hydrogen pressure in the container at approx. 1.0 MPa. The reaction selectivity is normally around 90 to 100%.

After the reaction, the catalyst is separated from the obtained reaction mixture using a normal method, and if necessary, the solvent, and the secondary amine generated by the hydrogenolysis reaction, are distilled at normal pressure or under decompression from the reaction liquid from which the catalyst has been removed, after which a crystallization solvent is added to the remaining reaction liquid to cause the target to precipitate as crystal, and then filtration or other method is used to obtain the target at high purity. Alternatively, the solvent is distilled at normal pressure or under decompression from the reaction liquid from which the catalyst has been removed, after which a crystallization solvent is added and simultaneously an acid such as aqueous acetic acid solution is added to neutralize the eliminated secondary amine base. Then, the water layer is separated and the target is caused to precipitate as crystal from the obtained organic layer, after which filtration or other method is used to separate and refine the target poly(ortho-methylphenol) to obtain a poly(ortho-methylphenol) of high purity.

Under the production method proposed by an embodiment of the present invention, the liquid containing the secondary amine, which is in turn contained in the distillate obtained from the aforementioned refinement step and/or the filtrate from the crystallization liquid obtained from the aforementioned step, may be used again directly, or after refining, as the material secondary amine in the first step. In other words, the secondary amine can be used cyclically.

Therefore, an embodiment of the present invention produces the target poly(ortho-methylphenol) at high yield and purity in a simple process based on reaction conditions that can be easily implemented through industrial processes, by causing a secondary amine and formaldehyde to react with a polyphenol to obtain a poly(ortho-aminomethyl)phenol (first step), and then breaking down the aminomethyl group of the obtained poly(ortho-aminomethyl)phenol by means of hydrogenolysis in the presence of a hydrogenation catalyst (second step).

EXAMPLES

Embodiments of the present invention are explained below by using examples. It should be noted, however, that the present invention is not at all limited to these examples.

Example 1

Production of 3,3'-dimethyl-4,4'-dihydroxydiphenyl ether (abbreviated as "DM-DHPE")

(First Step)
Into a one-liter four-way flask equipped with an agitator, temperature gauge and drip funnel, 50.5 g (0.25 mol) of 4,4'-dihydroxydiphenyl ether (abbreviated as "DHPE") and 81.3 g of toluene were introduced, after which, under agitation, 47.9 g (0.55 mol) of morpholine was drip-fed over a period of 30 minutes at 25° C. After the entire morpholine had been added, the temperature in the flask was raised to 80° C. and while maintaining this temperature 45.0 g (0.25 mol) of 35% formalin was drip-fed over a period of 1 hour. After the entire formalin had been added, the mixture was agitated continuously at the same temperature to cause crystal to precipitate. After 8 hours of agitation in this condition, 6.5 g (0.075 mol) of morpholine and 6.4 g (0.075 mol) of 35% formalin were drip-fed further over a period of 10 minutes. Thereafter, the mixture was agitated further at the same temperature to cause reaction for 8 hours. When the obtained reaction mixture was analyzed by high performance liquid chromatography (abbreviated as "HPLC"), the reaction ratio of material DHPE was 100%, while the selectivity of produced 3,3'-di(morpholino methyl)-4,4'-dihydroxy diphenyl ether (abbreviated as "DAM-DHPE") with respect to DHPE was 81.2%.

The reaction mixture was then gradually cooled and the precipitated crystal was filtered and dried to obtain 73.1 g of reaction product DAM-DHPE as white crystal. Its purity was 97.1% (based on HPLC analysis), while the yield with respect to DHPE was 71 mol %.

DAM-DHPE identification data
Proton NMR analysis (400 MHz, DMSO-d6 solvent)

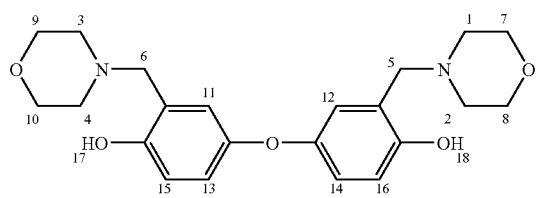

TABLE 1

| δ (ppm) | Assignment | Signal | Number of protons |
|---|---|---|---|
| 2.41~2.42 | 1~4 | t | 8 |
| 3.52 | 5~6 | s | 4 |

TABLE 1-continued

| δ (ppm) | Assignment | Signal | Number of protons |
|---|---|---|---|
| 3.56~3.59 | 7~10 | t | 8 |
| 6.70~6.71 | 11~14 | s & d | 4 |
| 6.76~6.77 | 15~16 | d | 2 |
| 9.87 | 17~18 | s | 2 |

(Second Step)

Into a one-liter autoclave equipped with an agitator and temperature gauge, 60.0 g (0.146 mol) of 3,3'-di(morpholinomethyl)-4,4'-dihydroxydiphenyl ether obtained by the reaction in the aforementioned first step was introduced together with 180 g of 2-propanol and 0.6 g of 10% carbon-supported palladium catalyst (wet product), after which the air in the container was replaced with nitrogen at room temperature, and then the nitrogen in the container was replaced with hydrogen. Thereafter, the temperature was raised to a range of 110 to 140° C., and while blowing in hydrogen to maintain the internal pressure within a range of 0.86 to 1.34 MPa (gauge pressure) the mixture was reacted for 6 hours under agitation.

When the obtained reaction mixture was analyzed by high performance liquid chromatography, the reaction ratio of DAM-DHPE was 100%, while the selectivity of target DM-DHPE with respect to DAM-DHPE was 92.9%.

After the reaction, the catalyst was filtered and removed from the obtained reaction mixture, and the remaining mixture was transferred into a one-liter four-way flask equipped with an agitator, temperature gauge and distillation tube. Next, nitrogen was introduced into the flask and the flask temperature was raised under nitrogen flow to distill 2-propanol and morpholine from the reaction mixture from which the catalyst had been removed, after which methyl ethyl ketone was added. The mixture containing methyl ethyl ketone was neutralized with aqueous hydrochloric acid solution, after which the water layer was separated, and the obtained oil layer was washed in water. Methyl ethyl ketone was distilled from the oil layer that had been washed in water, after which toluene was added. The mixture was then cooled and the precipitated crystal was filtered and dried to obtain 28.8 g of target 3,3'-dimethyl-4,4'-dihydroxydiphenyl ether (having a purity of 96% based on high performance liquid chromatography analysis) as powder crystal. Its yield with respect to material DAM-DHPE was 82.3 mol %.

DM-DHPE identification data

Proton NMR analysis (400 MHz, DMSO-d6 solvent)

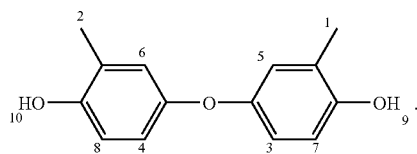

TABLE 2

| δ (ppm) | Assignment | Signal | Number of protons |
|---|---|---|---|
| 2.08 | 1~2 | s | 6 |
| 6.56~6.60 | 3~4 | d | 2 |
| 6.68 | 5~6 | s | 2 |

TABLE 2-continued

| δ (ppm) | Assignment | Signal | Number of protons |
|---|---|---|---|
| 6.71~6.73 | 7~8 | d | 2 |
| 9.03 | 9~10 | s | 2 |

Example 2

Production of 3,3'-dimethyl-4,4'-dihydroxydiphenyl ketone (abbreviated as "DM-DHPK")

(First Step)

Into a one-liter four-way flask equipped with an agitator, temperature gauge and drip funnel, 53.5 g (0.25 mol) of 4,4'-dihydroxydiphenyl ketone ("DHPK") and 86.1 g of toluene were introduced, after which, under agitation, 47.9 g (0.55 mol) of morpholine was drip-fed over a period of 30 minutes at room temperature. After the entire morpholine had been added, the temperature in the flask was raised to 80° C. and while maintaining this temperature 45.0 g (0.525 mol) of 35% formalin was drip-fed over a period of 1 hour.

After the entire formalin had been added, the mixture was agitated continuously for 6 hours at the same temperature, and then 6.5 g (0.075 mol) of morpholine and 6.4 g (0.075 mol) of 35% formalin were drip-fed further over a period of 10 minutes. Then, the mixture was agitated further for 3 hours at the same temperature, and then 6.5 g (0.075 mol) of morpholine and 6.4 g (0.075 mol) of 35% formalin were drip-fed further over a period of 10 minutes. Thereafter, the mixture was agitated further for 3 hours at the same temperature to complete the reaction.

When the obtained reaction mixture was analyzed by HPLC, the reaction ratio of DHPK was 100%, while the selectivity of produced 3,3'-di(morpholinomethyl)-4,4'-dihydroxydiphenyl ketone ("DAM-DHPK") with respect to DHPK was 61.1%.

The reaction mixture was then gradually cooled and the precipitated crystal was filtered and removed to obtain a filtrate containing the reaction product.

The obtained filtrate was decompressed and condensed by an evaporator to obtain 51.4 g of DAM-DHPK as ocher-colored soft solid. Its yield with respect to DHPK was 44.6 mol %, while the purity was 89.4% (based on HPLC analysis) and molecular weight was 411 (M-H)⁻ (based on mass spectrometry).

(Second Step)

Into a one-liter autoclave equipped with an agitator and temperature gauge, 51.4 g of 3,3'-di(morpholinomethyl)-4,4'-dihydroxydiphenyl ketone obtained in the first step was introduced together with 154.2 g of 2-propanol and 0.8 g of 10% carbon-supported palladium catalyst (wet product), after which the air in the container was replaced with nitrogen at room temperature, and then the nitrogen in the container was replaced with hydrogen. Thereafter, the temperature was raised to 110° C., and while blowing in hydrogen to maintain the internal pressure within a range of 0.98 to 1.0 MPa the mixture was reacted for 6 hours under agitation.

When the obtained reaction mixture was analyzed by high performance liquid chromatography, the reaction ratio of DAM-DHPK was 100%, while the selectivity of DM-DHPK with respect to DAM-DHPK was 77.8%.

After the catalyst had been filtered and removed from the obtained reaction mixture, the remaining mixture was transferred into a one-liter four-way flask equipped with an agitator, temperature gauge and distillation tube. Next, nitrogen was introduced into the flask and the flask temperature was raised under nitrogen flow to distill 2-propanol and morpholine from the reaction mixture from which the catalyst had been removed, after which methyl ethyl ketone was added. The mixture containing methyl ethyl ketone was neutralized with aqueous hydrochloric acid solution, after which the water layer was separated, and the obtained oil layer was washed in water. Methyl ethyl ketone was distilled from the oil layer that had been washed in water, after which toluene was added. The mixture was then cooled and the precipitated crystal was filtered. The obtained crude crystal was dissolved in methyl isobutyl ketone under heat, and then the temperature was brought down. The precipitated crystal was filtered and dried to obtain 4.7 g of target 3,3'-dimethyl-4,4'-dihydroxydiphenyl ketone as powder crystal. Its purity based on high performance liquid chromatography analysis was 89.8%, while the yield with respect to DAM-DHPK was 15.6 mol %.

DM-DHPK identification data

Molecular weight (mass spectrometry): 241 (M-H)⁻.

Proton NMR analysis (400 MHz, DMSO-d6 solution)

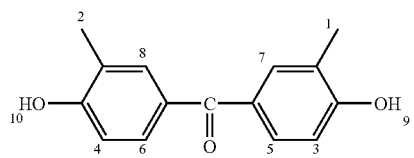

TABLE 3

| δ (ppm) | Assignment | Signal | Number of protons |
|---|---|---|---|
| 2.15 | 1~2 | s | 6 |
| 6.85~6.88 | 3~4 | d | 2 |
| 7.38~7.41 | 5~6 | d | 2 |
| 7.47 | 7~8 | s | 2 |
| 10.12 | 9~10 | s | 2 |

Example 3

Production of tris(3-methyl-4-hydroxyphenyl)methane (First Step)

Into a four-way flask equipped with an agitator, temperature gauge and drip funnel, 43.8 g (0.15 mol) of tris(4-hydroxyphenyl)methane and 70.1 g of toluene were introduced, after which, under agitation, 43.1 g (0.495 mol) of morpholine was drip-fed over a period of 30 minutes at 25° C. Thereafter the temperature in the flask was raised to 40° C. and while maintaining the temperature within a range of 39 to 45° C. 40.5 g (0.473 mol) of 35% formalin was drip-fed over a period of 1 hour. The mixture was agitated continuously while maintaining the temperature in the flask within a range of 40 to 42° C. to cause crystal to precipitate.

The mixture was agitated continuously for 16 hours in this condition, and then 5.9 g (0.068 mol) of morpholine and 5.8 g (0.068 mol) of 35% formalin were drip-fed further over a period of 10 minutes, and the mixture was agitated for 6 hours at the same temperature to complete the reaction.

When the obtained reaction mixture was analyzed by HPLC, the reaction ratio of tris(4-hydroxyphenyl)methane was 100%, while the selectivity of produced tris(4-hydroxy-3-morpholinomethylphenyl)methane with respect to tris(4-hydroxyphenyl)methane was 63.9%.

The reaction mixture was then gradually cooled and the precipitated crystal was filtered and dried to obtain 59.0 g of tris(4-hydroxy-3-morpholinomethylphenyl)methane as white crystal. Its yield with respect to tris(4-hydroxyphenyl)methane was 57 mol %, while the purity based on HPLC was 85.2%.

Next, the obtained crude crystal was further crystallized and refined by toluene to obtain, as white crystal, 37.4 g of tris(4-hydroxy-3-morpholinomethylphenyl)methane with a HPLC purity of 93.6%.

Tris(4-hydroxy-3-morpholinomethylphenyl)methane identification data

Molecular weight (mass spectrometry): 588 (M-H)⁻.

Proton NMR analysis (400 MHz, DMSO-d6 solution)

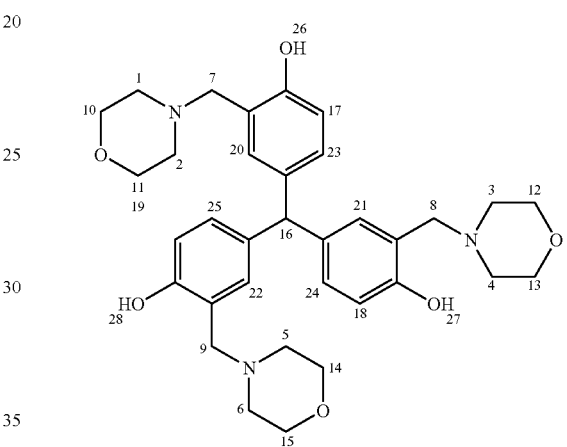

TABLE 4

| δ (ppm) | Assignment | Signal | Number of protons |
|---|---|---|---|
| 2.54 | 1~6 | t | 12 |
| 3.62 | 7~9 | s | 6 |
| 3.74 | 10~15 | t | 12 |
| 5.21 | 16 | s | 1 |
| 6.67~6.73 | 17~22 | s & d | 6 |
| 6.82~6.85 | 23~25 | d | 3 |
| 10.53 | 26~28 | s | 3 |

(Second Step)

Into a one-liter autoclave equipped with an agitator and temperature gauge, 36.7 g of tris(4-hydroxy-3-morpholinomethylphenyl)methane with a purity of 93.6% (based on HPLC analysis), as obtained in the aforementioned first step, was introduced together with 146.8 g of 2-propanol and 0.4 g of 10% carbon-supported palladium catalyst (wet product), after which the air in the container was replaced with nitrogen at room temperature, and then the nitrogen in the container was replaced with hydrogen. Thereafter, the temperature was raised to 127° C., and while blowing in hydrogen to maintain the internal pressure within a range of 1.28 to 1.32 MPa (gauge pressure) and keeping the temperature within a range of 127 to 130° C. the mixture was reacted for 3 hours under agitation.

When the obtained reaction mixture was analyzed by HPLC, the reaction ratio of tris(4-hydroxy-3-morpholinomethylphenyl)methane was 100%, while the selectivity of target tris(3-methyl-4-hydroxyphenyl)methane with respect to tris(4-hydroxy-3-morpholinomethylphenyl)methane was 99.2%.

After the catalyst had been filtered and removed from the obtained reaction mixture, the remaining mixture was transferred into a one-liter four-way flask equipped with an agitator, temperature gauge and distillation tube. Next, nitrogen was introduced into the flask and the flask temperature was raised under nitrogen flow to distill 2-propanol and morpholine from the reaction mixture from which the catalyst had been removed, after which methyl ethyl ketone was added. The mixture containing methyl ethyl ketone was neutralized with aqueous hydrochloric acid solution, after which the water layer was separated, and the obtained oil layer was washed in water. Methyl ethyl ketone was distilled from the oil layer that had been washed in water, after which toluene and methyl isobutyl ketone were added. The mixture was then cooled and the precipitated crystal was filtered to obtain 17.7 g of target tris(3-methyl-4-hydroxyphenyl)methane as powder crystal. Its purity based on high performance liquid chromatography analysis was 94.2%, while the yield with respect to material tris(4-hydroxy-3-morpholinomethylphenyl)methane was 85.6 mol %.

Tris(3-methyl-4-hydroxyphenyl) identification data
Molecular weight (mass spectrometry): 333 (M-H)
Proton NMR analysis (400 MHz, DMSO-d6 solution)

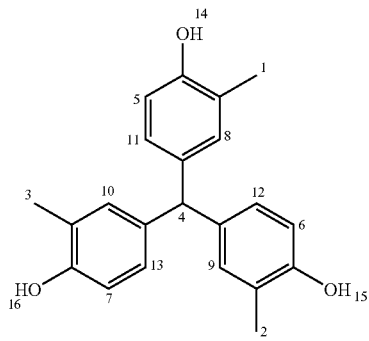

TABLE 5

| δ (ppm) | Assignment | Signal | Number of protons |
|---|---|---|---|
| 2.05 | 1~3 | s | 9 |
| 5.12 | 4 | s | 1 |
| 6.67~6.77 | 5~13 | s & d | 9 |
| 9.06 | 14~16 | s | 3 |

Although all possible variations are not listed herein, the present invention can be embodied in any modes incorporating various changes, modifications and improvements based on the knowledge of those skilled in the art. It goes without saying that these embodiments are also included in the scope of the present invention, as long as they do not deviate from the purpose of the present invention. Therefore, it should be clearly understood that the forms of the present invention are illustrative only and are not intended to limit the scope of the present invention.

In the present disclosure where conditions and/or structures are not specified, the skilled artisan in the art can readily provide such conditions and/or structures, in view of the present disclosure, as a matter of routine experimentation.

The present application claims priority to Japanese Patent Application No. JP2006-030185, filed Feb. 7, 2006, the disclosure of which is incorporated herein by reference in its entirety.

What is claimed is:
1. A method of producing a poly(ortho-methylphenol) represented by general formula (2) comprising the steps of:
    reacting a polyphenol compound represented by general formula (1) with formaldehyde in the presence of a secondary amine, thereby obtaining a poly(ortho-aminomethyl)phenol; and
    hydrogenolyzing the amino methyl group of the poly(ortho-aminomethyl)phenol in the presence of a hydrogenation catalyst:

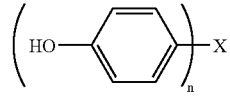

General formula (1)

wherein X represents a —O— group, —S— group, carbonyl group, aromatic hydrocarbon group, or saturated hydrocarbon group of carbon number 1 to 12, and n represents an integer of 2 to 4,

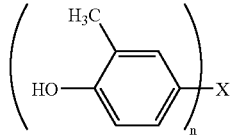

General formula (2)

wherein X and n represent the same as in general formula (1).

2. The method according to claim 1, wherein the formaldehyde is used in a range of from moles equivalent to the moles of the hydroxyl group in the polyphenol compound (n moles in the general formula (1)) to twice the moles of the hydroxyl group in the polyphenol compound per one mole of the polyphenol compound.

3. The method according to claim 1, wherein the secondary amines is used in a range of from moles equivalent to the moles of the hydroxyl group in the polyphenol compound (n moles in general formula (1)) to twice the moles of the hydroxyl group in the polyphenol per one mole of the polyphenol compound.

4. The method according to claim 1, wherein a mole ratio of the secondary amine and the formaldehyde is 1:1 to 1.2:1.

5. The method according to claim 1, wherein a solvent is used in the reacting step.

6. The method according to claim 1, wherein a reaction temperature in the reacting step is in a range of −50° C. to 150° C.

7. The method according to claim 1, wherein the hydrogenation catalyst is used in a range of 0.5 to 10 parts by weight with respect to 100 parts by weight of the poly(ortho-aminomethyl)phenol in the hydrogenolyzing step.

8. The method according to claim 1, wherein an acid component is used as a co-catalyst in a range of 0.01 to 100 parts by weight with respect to 100 parts by weight of the poly(ortho-aminomethyl)phenol in the hydrogenolyzing step.

9. The method according to claim 1, wherein the hydrogenolysis reaction is carried out at temperatures in a range of 20 to 180° C. and at hydrogen pressures in a range of 0.1 to 1.5 MPa as gauge pressure.

10. The method according to claim 9, wherein the reaction time of the hydrogenolysis reaction is in a range of 0.5 to 20 hours.

11. The method according to claim 9, wherein a solvent is used in the hydrogenolysis reaction.

12. The method according to claim 11, wherein the solvent is an organic acid or alcohol.

* * * * *